(12) United States Patent
Yoo et al.

(10) Patent No.: US 10,010,849 B2
(45) Date of Patent: Jul. 3, 2018

(54) APPARATUS FOR GENERATING 1-METHYLCYCLOPROPENE

(75) Inventors: Sang Ku Yoo, Gyeonggi-do (KR); Jin Wook Chung, Seoul (KR)

(73) Assignee: ERUM BIOTECHNOLOGIES, INC., Suwon (KR)

( * ) Notice: Subject to any disclaimer, the term of this patent is extended or adjusted under 35 U.S.C. 154(b) by 1180 days.

(21) Appl. No.: 14/007,951

(22) PCT Filed: Mar. 20, 2012

(86) PCT No.: PCT/KR2012/001970
§ 371 (c)(1),
(2), (4) Date: Sep. 26, 2013

(87) PCT Pub. No.: WO2012/134088
PCT Pub. Date: Oct. 4, 2012

(65) Prior Publication Data
US 2014/0017134 A1 Jan. 16, 2014

(30) Foreign Application Priority Data

Mar. 30, 2011 (KR) .................. 10-2011-0029038
Feb. 16, 2012 (KR) .................. 10-2012-0015891

(51) Int. Cl.
| | |
|---|---|
| *B01J 8/00* | (2006.01) |
| *B01J 19/00* | (2006.01) |
| *B01J 10/00* | (2006.01) |
| *B01J 14/00* | (2006.01) |
| *B01J 15/00* | (2006.01) |
| *B01J 19/24* | (2006.01) |
| *B01J 4/00* | (2006.01) |
| *C07C 1/32* | (2006.01) |

(52) U.S. Cl.
CPC .............. *B01J 14/00* (2013.01); *B01J 4/001* (2013.01); *B01J 10/00* (2013.01); *B01J 19/24* (2013.01); *C07C 1/321* (2013.01); *B01J 2204/002* (2013.01); *C07C 2601/02* (2017.05)

(58) Field of Classification Search
CPC ... B01J 10/00; B01J 12/00; B01J 14/00; B01J 16/00; B01J 19/00; B01J 8/00; B01J 15/00
USPC ........................................................ 422/129
See application file for complete search history.

(56) References Cited

U.S. PATENT DOCUMENTS

| | | |
|---|---|---|
| 6,017,849 A | 1/2000 | Daly et al. |
| 6,161,725 A | 12/2000 | Dean |
| 2003/0220201 A1 | 11/2003 | Kostansek et al. |

(Continued)

FOREIGN PATENT DOCUMENTS

| | | |
|---|---|---|
| KR | 10-2006-0116371 A | 11/2006 |
| KR | 10-2007-0053113 A | 5/2007 |

OTHER PUBLICATIONS

Chan, T.H. and D. Massuda, "Entry into the Cyclopropene System via Vinylsilanes", *Tetrahedron Letters*, vol. 16, No. 39, (Aug. 22, 1975), pp. 3383-3386.

(Continued)

*Primary Examiner* — Huy Tram Nguyen
(74) *Attorney, Agent, or Firm* — Kilpatrick Townsend & Stockton LLP

(57) ABSTRACT

Provided is an apparatus for generating 1-methylcyclopropene. The apparatus of the present invention may enable the immediate and convenient generation of 1-methylcyclopropene in a desired location using stable 1-methylcyclopropene precursors.

13 Claims, 3 Drawing Sheets

(56) References Cited

U.S. PATENT DOCUMENTS

2008/0251016 A1* 10/2008 Cunning ............. C23C 16/4481
                                                              118/722
2008/0286426 A1* 11/2008 Yoo ........................ A23B 7/154
                                                              426/321

OTHER PUBLICATIONS

Billups, W. E. and Michael M. Haley, "Spiropentadiene", *Journal of the American Chemical Society*, vol. 113, No. 13, (Jun. 1, 1991), pp. 5084-5085.
Billups, W. E., Gon-Ann Lee, Benny E. Arney Jr., and Kenton H. Whitmire, "1,3-Bridged Cyclopropenes", *Journal of the American Chemical Society*, vol. 113, No. 21, (Oct. 1, 1991), pp. 7980-7984.
Haley, Michael M., Bluegrass Biggs, Will A. Looney, and Robert D. Gilbertson, "Synthesis of Alkenyl- and Alkynylcyclopropenes", *Tetrahedron Letters*, vol. 36, No. 20, (May 15, 1995), pp. 3457-3460.
Mizojiri, Ryo, Hirokazu Urabe, and Fumie Sato, "Generation of a Silylethylene-Titanium Alkoxide Complex. A Versatile Reagent for Silylethylation and Silylethylidenation of Unsaturated Compounds", *The Journal of Organic Chemistry*, vol. 65, No. 19, (Sep. 15, 2000), pp. 6217-6222. Supporting Information pp. 1-14 included.
Banwell Martin G., Madelaine Corbett, Jacqueline Gulbis, Maureen F. Mackay, and Monica E. Reum, "Generation and Solution-phase Behaviour of Some 2-Halogeno-1,3-ring-fused Cyclopropenes", *Journal of the Chemical Society*, Perkin Transactions 1, No. 8 (1993), pp. 945-963.
PCT Search Report and Written Opinion dated Oct. 24, 2012 for Int'l Patent Application No. PCT/KR/2012/001970, 9 pages.

* cited by examiner

APPARATUS FOR GENERATING 1-METHYLCYCLOPROPENE

CROSS-REFERENCE TO RELATED APPLICATIONS

This application is the National Phase of International Application No. PCT/KR2012/001970, filed Mar. 20, 2012, which claims priority to KR Patent Application No. 10-2011-0029038, filed Mar. 30, 2011, and KR Patent Application No. 10-2012-0015891, filed Feb. 16, 2012, the disclosures of which are incorporated by reference in their entirety.

TECHNICAL FIELD

One or more embodiments of the present invention relate to an apparatus for generating 1-methylcyclopropene, and more particularly, to an apparatus for generating 1-methylcyclopropene in a target site.

BACKGROUND ART

Cyclopropene derivatives such as 1-methylcyclopropene (1-MCP) are inhibitors inhibiting the action of ethylene, which is a plant hormone that promotes ripening of fruits, flowers, vegetables, and the like, and the inhibiting effects thereof are known to be excellent.

In particular, 1-MCP is present in a gaseous state at room temperature, and thus, the inside of agricultural products warehouses can be easily treated with 1-MCP. However, cyclopropene compounds such as 1-MCP easily undergo polymerization and thus it is not easy to store such cyclopropene compounds for a long-term period by using a general method.

U.S. Pat. No. 6,017,849 discloses a method of incorporating these cyclopropene compounds into a molecular encapsulation agent for storage, for example by adsorbing 1-MCP onto a molecular encapsulation agent, e.g., α-cyclodextrin. However, this method requires storage in the form of a complex formed by adsorbing 1-MCP onto α-cyclodextrin. In addition, when used, the complex needs to contact with a solvent so that 1-MCP is dissolved and released in the solvent, which leads to complicated processes and requires know-how of treatment of these compounds.

DETAILED DESCRIPTION OF THE INVENTION

Technical Problem

The present invention provides an apparatus for generating 1-methylcyclopropene (1-MCP) for conveniently preparing and spraying 1-MCP in an agricultural site.

Technical Solution

According to an aspect of the present invention, there is provided an apparatus for generating 1-methylcyclopropene including: a first vessel including a 1-methylcyclopropene precursor; a second vessel including a fluoride ion-containing compound solution that reacts with the 1-MCP precursor to produce 1-methylcyclopropene; and a carrier gas that is introduced into any one of the first vessel and the second vessel to transfer any one of the 1-methylcyclopropene precursor and the fluoride ion-containing compound solution into the other of the first vessel and the second vessel so that the 1-methylcyclopropene precursor and the fluoride ion-containing compound solution react with each other, wherein as the carrier gas moves from any one of the first vessel and the second vessel to the other thereof, the carrier gas discharges a reaction product including 1-methylcyclopropene produced in the other of the first vessel and the second vessel to the outside.

The apparatus may further include a third vessel including a filter for removing byproducts except for 1-methylcyclopropene from the reaction product.

Advantageous Effects

According to the one or more embodiments of the present invention, transfer and mixing of reactants and discharge of a resultant reaction product are performed in an apparatus for generating 1-MCP by using a carrier gas in one direction within a short time. Thus, by using the apparatus for generating 1-MCP, 1-MCP may be conveniently prepared and used in a target site.

MODE OF THE INVENTION

Exemplary embodiments of the invention will now be described more fully with reference to the accompanying drawings.

According to an embodiment of the present invention, an apparatus for generating 1-MCP includes a first vessel including a 1-MCP precursor; a second vessel including a fluoride ion-containing compound solution that reacts with the 1-MCP precursor to produce 1-MCP; and a carrier gas that is introduced into any one of the first vessel and the second vessel to transfer any one of the 1-MCP precursor and the fluoride ion-containing compound solution into the other of the first vessel and the second vessel so that the 1-MCP precursor and the fluoride ion-containing compound solution react with each other, wherein as the carrier gas moves from any one of the first vessel and the second vessel to the other thereof, the carrier gas discharges a resultant reaction product including 1-MCP produced in the other of the first vessel and the second vessel to the outside of the vessel.

Specifically, in the 1-MCP generating apparatus, the 1-MCP precursor and the fluoride ion-containing compound solution are contained in the first vessel and the second vessel, respectively. At a time when 1-MCP is needed, a carrier gas is supplied to any one of the first vessel and the second vessel to transfer any one of the 1-MCP precursor and the fluoride ion-containing compound solution to the other thereof, so that the 1-MCP precursor and the fluoride ion-containing compound solution are mixed to induce a reaction therebetween. A resultant reaction product including the produced 1-MCP is discharged by the carrier gas to the outside of the vessel.

In a 1-MCP generating apparatus according to one embodiment of the invention, transfer of reactants, mixing and reaction of the reactants, and discharge of a resultant reaction product may be performed in an integrated manner by using a carrier gas. Therefore, 1-MCP with low storage stability may be directly prepared and conveniently used in a target site by using the 1-MCP generating apparatus.

Figure 1A:
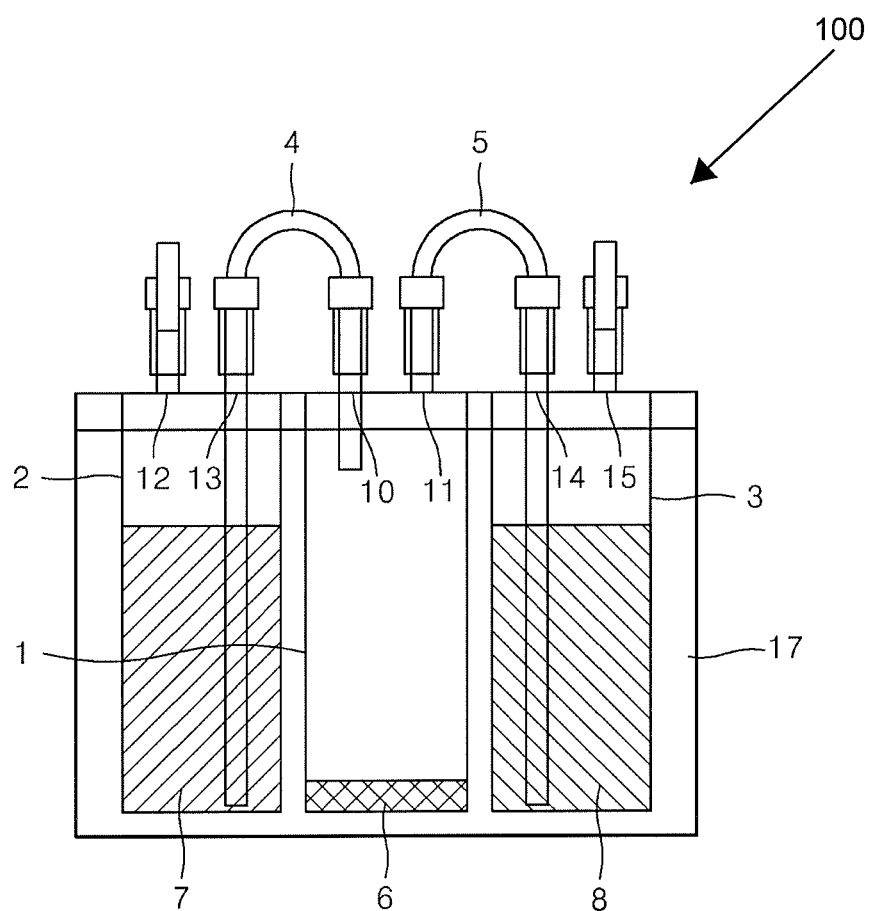
FIG. 1A is a diagram illustrating an apparatus for generating 1-MCP according to an embodiment of the present invention in which a 1-MCP precursor and a fluoride ion-containing compound solution are contained in a first vessel and a second vessel, respectively.
Figure 1B:
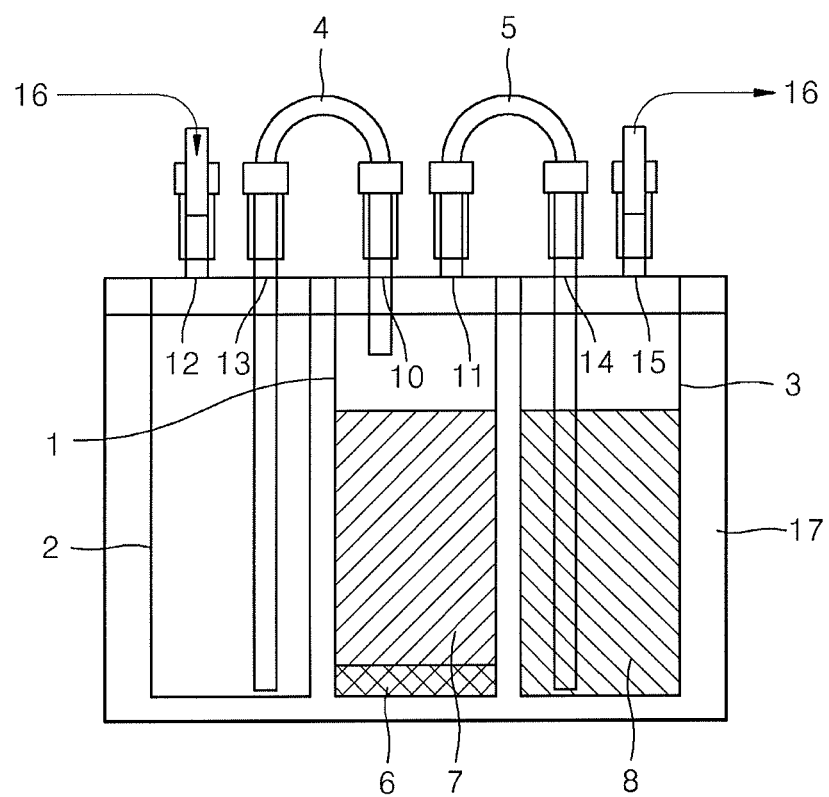
FIG. 1B is a diagram illustrating a 1-MCP generating apparatus according to an embodiment of the present invention in which a 1-MCP precursor and a fluoride ion-containing compound solution are mixed.
Figure 1C:
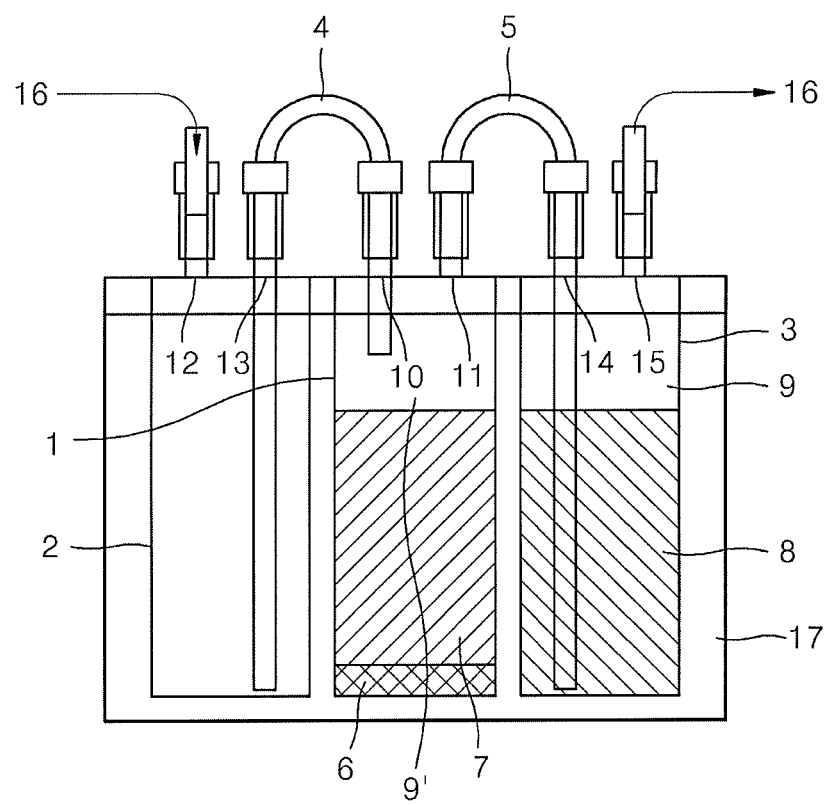
FIG. 1C is a diagram for explaining a process of discharging the produced 1-MCP from a 1-MCP generating apparatus according to an embodiment of the present invention.

FIGS. 1A through 1C are diagrams illustrating a structure and an operation of a 1-MCP generating apparatus 100 according to an embodiment of the present invention. In the drawings, like reference numerals denote like elements of the 1-MCP generating apparatus 100.

FIG. 1A is a drawing illustrating a state in which a fluoride ion-containing compound solution 7 and a 1-MCP precursor 6 are contained in a first vessel 1 and a second vessel 2, respectively. FIG. 1B is a drawing illustrating a state in which the 1-MCP precursor 6 and the fluoride ion-containing compound solution 7 are mixed. FIG. 1C is a drawing illustrating a state in which produced 1-MCP 9 is discharged.

In the present embodiments, to filter byproducts except for 1-MCP from the resultant reaction product, the 1-MCP generating apparatus 100 further includes a third vessel 3 including a filter 8 through which the resultant reaction product passes. In this case, only the 1-MCP 9 is discharged by a carrier gas 16 from the filter included in the third vessel 3 to the outside of the third vessel 3, and the remaining byproducts remain in the filter 8.

A 1-MCP generating apparatus according to one embodiment of the present invention may further include a case 17 in which the first vessel 1 and the second vessel 2, and the third vessel 3, if included, are mounted.

FIG. 1A illustrates a state before the 1-MCP generating apparatus 100 operates. In this example, when a carrier gas 16, for example, air is supplied to the second vessel 2, the fluoride ion-containing compound solution 7 of the second vessel 2 is transferred to the first vessel 1 to be mixed with the 1-MCP precursor 6 contained in the first vessel 1, as illustrated in FIG. 1B, and a resultant reaction product 9' including 1-MCP starts to be produced from the mixing process, as illustrated in FIG. 1C. The resultant reaction product 9' including 1-MCP passes through the filter 8 of the third vessel 3 by the carrier gas 16. In the third vessel 3, the 1-MCP 9 passes through the filter 8 without inducing any reaction, and extra byproducts undergo decomposition or polymerization, thereby being converted to water-soluble materials and removed.

The first vessel 1, the second vessel 2, and the third vessel 3, if included, may be detachably attached. That is, the first vessel 1 and the second vessel 2 that respectively hold the 1-MCP precursor 6 and the fluoride ion-containing compound solution 7 remain closed, at a time when 1-MCP is needed the first and second vessels 1 and 2 are coupled with a cap unit (not shown) included in the 1-MCP generating apparatus 100, and the carrier gas 16 is supplied to any one of the first vessel 1 and the second vessel 2 through a tube (not shown), thereby initiating a reaction between the 1-MCP precursor 6 and the fluoride ion-containing compound solution 7. After the reaction is completed, the first vessel 1 and the second vessel 2 may be detached from the cap unit and materials remaining inside the first and second vessels 1 and 2 may be removed. When used again, the first and second vessels 1 and 2 are filled with the 1-MCP precursor 6 and the fluoride ion-containing compound solution 7, respectively and the processes described above are repeatedly performed, thereby generating 1-MCP.

In FIGS. 1A through 1C, it is illustrated that the carrier gas 16 travels in this order from the second vessel 2 to the first vessel 1 to the third vessel 3. However, the transfer order of the carrier gas 16 is not limited to the above example. For example, the carrier gas 16 may travel in this order from the first vessel 1 to the second vessel 2 to the third vessel 3. In this case, the 1-MCP precursor 6 contained in the first vessel 1 is moved to the second vessel 2 to react with the fluoride ion-containing compound solution 7 included therein, thereby generating 1-MCP.

In this regard, the volume of 1-MCP precursor is relatively smaller than the volume of fluoride ion-containing compound solution (⅓ to ⅕) and there is a direct correlation between the amount of 1-MCP precursor and the amount of 1-MCP generated. The fluoride ion-containing compound solution is used in an equivalent weight or more (generally, 1 to 3 equivalent weights of a 1-MCP precursor), and thus it is more desirable that the fluoride ion-containing compound solution included in the second vessel is moved to the first vessel including the 1-MCP precursor to react with the 1-MCP precursor.

The fluoride ion-containing compound solution may be prepared by dissolving a fluoride ion-containing compound in a solvent. The solvent is not particularly limited as long as it dissolves the fluoride ion-containing compound. Specifically, the solvent may be a polar and aprotic solvent, such as DMF, DMSO, dimethylacetamide, 1-methyl-2-pyrrolidone, or the like.

The 1-MCP precursor is in a liquid state, and thus may be used as it is without dissolving the 1-MCP precursor in a separate solvent. However, if there is a need to accurately produce a small amount of 1-MCP, the 1-MCP precursor may be diluted using a solvent and then used after accurately measuring the amount thereof.

The fluoride ion-containing compound solution 7 contained in the second vessel 2 is moved by the carrier gas 16 to the first vessel 1 and then mixed with the 1-MCP precursor 6 contained in the first vessel 1 to induce a reaction therebetween. In this regard, the carrier gas 16 may not only transfer the fluoride ion-containing compound solution 7 but also facilitate better mixing of the fluoride ion-containing compound solution 7 and the 1-MCP precursor 6. The produced 1-MCP becomes unstable as it is concentrated. In the 1-MCP generating apparatus 100, however, 1-MCP is discharged by a carrier gas immediately after produced and thus problems such as polymerization of 1-MCP may not occur. In other words, all the processes in the 1-MCP generating apparatus 100 may be performed using only the pressure of the carrier gas for discharging 1-MCP.

The carrier gas 16 may be supplied to the second vessel 2, the first vessel 1, and the third vessel 3 without using separate intermediate valves so that transfer of reactants, reaction therebetween, and discharge and purification of a resultant reaction product may be performed in an integrated manner within a short time.

The first vessel 1, the second vessel 2, and the third vessel 3, if included, may respectively include inlets 10, 12 and 14 and respectively include outlets 11, 13 and 15. The first vessel 1, the second vessel 2, and the third vessel 3, if included, may be connected to each other through a tube. That is, the first vessel 1 and the second vessel 2 are connected to each other through a first tube 4, and the first vessel 1 and the third vessel 3 are connected to each other through a second tube 5. If necessary, the second vessel 2 and the third vessel 3 may be connected to each other through the second tube 5. The carrier gas 16 is supplied to the inside of the second vessel 2 through the inlet 12 of the second vessel 2 from an air compressor (not shown) via a tube (not shown) and then supplied to the first vessel 1 through the inlet 10 of the first vessel 1 via the first tube 4 through the outlet 13 of the second vessel 2. In addition, the carrier gas 16 is discharged to the outside of the first vessel 1 through the outlet 11 of the first vessel 1 via the second tube 5. If the 1-MCP generating apparatus 100 includes the third vessel 3, the carrier gas 16 is supplied to the third vessel 3 through the inlet 14 of the third vessel 3 and then discharged to the outside through the outlet 15 of the third vessel 3. Reactants are moved along the movement path of the carrier gas 16 as described above and a resultant reaction product is discharged therealong.

Materials and types of the first vessel and the second vessel of the 1-MCP generating apparatus are not particularly limited as long as they have a structure capable of stably storing used materials and, if necessary, discharging the produced materials. For example, the first vessel and the second vessel may be any vessel that includes an inlet and an outlet and is made of an inert material with respect to a material to be stored. In particular, the most widely used resins such as polyethylene and polypropylene may be used in terms of durability, light weight, and economical costs, and a fluorinated resin such as Teflon may be also used in terms of durability, light weight, handling convenience, and reliability.

In general, 1-MCP has a sufficient effect in air even at a low concentration of 1 ppm or less, and thus, approximately 0.01 to 5.0 l (0.45 to 220 mmole) of 1-MCP is needed to treat warehouses of 10 m$^3$~5,000 m$^3$. In the 1-MCP generating apparatus, the amount of 1-MCP precursor is in the range of about 50 mg to about 30 g, and the amount of fluoride ion-containing compound solution is in the range of about 0.1 ml to about 200 ml, and thus a vessel having a volume ranging from 1 ml to 500 ml may be used as a first vessel and a second vessel.

Tubes including the first tube 4 and the second tube 5 may have a different length in each vessel according to the phases of materials that are introduced into and discharged from each vessel.

In particular, since only the carrier gas 16 is introduced into the second vessel 2 through the inlet 12 of the second vessel 2, the inlet 12 may include a tube (not shown) having a length that reaches a certain position above a surface of the fluoride ion-containing compound solution 7 contained in the second vessel 2. In addition, since the outlet 13 of the second vessel 2 discharges the fluoride ion-containing compound solution 7, the outlet 13 may include the first tube 4 having a length that reaches the bottom of the second vessel 2. Also, the fluoride ion-containing compound solution 7 and the carrier gas 16 are introduced into the first vessel 1 through the inlet 10 and the resultant reaction product 9' including the produced 1-MCP is discharged through the outlet 11, and thus, the first tube 4 and the second tube 5 that are respectively included in the inlet 10 and the outlet 11 do not need to have a length that reaches the bottom of the first vessel 1.

The third vessel 3 may include the inlet 14 through which the resultant reaction product 9' including 1-MCP that has been discharged from the first vessel 1 is introduced and the outlet 15 through which the 1-MCP 9 is discharged. In this regard, the inlet 14 may include the second tube 5 having a length that reaches the filter 8 so that the resultant reaction product 9' is introduced therethrough, and the outlet 15 may include a tube (not shown) at a certain position above a surface of the filter 8.

The filter 8 included in the third vessel 3 removes reaction byproducts such as halosilane or acidic byproducts such as HF by decomposition or neutralization. For example, the filter 8 may be a filter made of one selected from a basic aqueous solution prepared by dissolving NaOH, KOH, $Na_2CO_3$, $NaHCO_3$, $K_2CO_3$, $KHCO_3$, $Na_2SiO_2$, $K_2SiO_2$, MeONa, EtONa, or iPrONa; basic short-chain alcohol solutions such as ethylene glycol, ethanol, methanol, and isopropanol; a sponge-type polymer and natural fiber that are impregnated with a basic aqueous solution or a basic short-chain alcohol solution; and inorganic materials such as silicate, alumina, mud, diatomite, lime, $CaCl_2$, zeolite, and molecular sieves.

The first vessel 1, in which a reaction actually occurs, may further include a thermostat as a heating device (not shown), in order to maintain a reaction rate constantly. Also, if a reaction occurs in the second vessel 2, the second vessel 2 may further include a thermostat as a heating device. A reaction temperature may be in the range of 10 to 60° C., for example, in the range of 20 to 50° C. If the reaction temperature is within the range described above, concerns about discharge of byproducts together with 1-MCP, due to evaporation of byproducts may be minimized and a separate cooling device is not needed.

The carrier gas used in the 1-MCP generating apparatus may be an inert gas such as nitrogen or air. The carrier gas may be supplied by a carrier gas supply unit (not shown) such as an air compressor that provides a pressurized gas. A flow rate of the carrier gas is not particularly limited. However, if the pressure of the air compressor is the same, a difference in flow rates may occur according to internal diameters of tubes made of polyethylene, polypropylene, or Teflon that connect the first vessel, the second vessel, and the filter. That is, as the internal diameter of a tube decreases, a flow rate in the tube becomes fast, and, as the internal diameter of a tube increases, a flow rate in the tube becomes slow. As the flow rate of the carrier gas in tubes increases, there is an increasing possibility of discharging impurities together with 1-MCP to the outside of the vessel, along the flow of air. However, if the internal diameter of the tube increases, the tube has less flexibility, and thus the tube is not suitable for use to connect vessels to one another. Therefore, when the volume of vessel is about 30 to 500 ml, the internal diameter of the tube that connects vessels may be in the range of about 1.5 to about 3.0 mm.

Assuming the volume of vessel is in the range of about 30 to about 500 ml and the internal diameter of tube that connects vessels is in the range of about 1.5 to about 3.0 mm, the carrier gas may be supplied to the first vessel or the second vessel at a flow rate of 2 ml to 3,000 ml/min. In this regard, if a large amount of 1-MCP is needed, the carrier gas may be supplied at a rapid flow rate, and, on the other hand, if a small amount of 1-MCP is needed, the carrier gas may be supplied at a slow flow rate.

The resultant reaction product including 1-MCP is in a gaseous state, and thus may be easily discharged into a space to be treated therewith without using separate additional elements such as nozzles.

The 1-MCP precursor used in the 1-MCP generating apparatus may be a β-halocyclopropylsilane derivative represented by Formula 1 below:

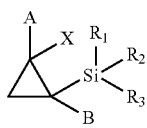

<Formula 1> where A is a methyl group;
B is a hydrogen atom;
X is a halogen atom; or a leaving group containing any one selected from an oxygen atom, a sulfur atom, a nitrogen atom, and a phosphorus atom; and
each of $R_1$, $R_2$, and $R_3$ is independently one of a hydrogen atom, a $C_1$-$C_{10}$ alkyl group, a $C_6$-$C_{10}$ aryl group, a $C_1$-$C_{10}$ alkoxy group, and a halogen atom.

In Formula 1, examples of the leaving group containing an oxygen atom include -$TOSO_2$—O—, $TO_2$—O—, TSO—O—, T-O—, TCO—O—, TOCO—O—, and TNHCO—O—.

Examples of the leaving group containing a sulfur atom include $TOSO_2$—, $TSO_2$—, TSO—, TS—, TOSO—, and TOS—.

Examples of the leaving group containing a nitrogen atom or a phosphorus atom include $T_3N^+$—, $T_2N$—, TNH—, $NH_2$—, $T_2P$—, $T_3P^+$—, $(TO)_2P$—, and $(TO)_2PO$—.

In these examples, T may be a $C_1$-$C_{10}$ alkyl group or a $C_6$-$C_{10}$ aryl group.

The fluoride ion-containing compound used in the 1-MCP generating apparatus may be a compound represented by Formula 2 below:

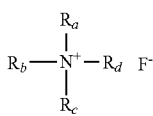

<Formula 2> where each of $R_a$, $R_b$, $R_c$, and $R_d$ is independently a $C_1$-$C_{20}$ alkyl group or a $C_6$-$C_{15}$ aryl group.

For example, the $C_1$-$C_{20}$ alkyl group may be methyl, ethyl, n-propyl, isopropyl, n-butyl, isobutyl, n-pentyl, n-hexyl, n-heptyl, n-octyl, or n-decyl.

For example, the $C_6$-$C_{15}$ aryl group may be phenyl or naphthyl.

The fluoride ion-containing compound may be used in a dissolved form in a solvent such as DMF, DMSO, or dimethylacetamide, rather than used alone. The solvent may be used in an amount of from 0.5 to 3.0 times the amount of the fluoride ion-containing compound, but if only a small amount of 1-MCP is needed, the solvent may be used in an amount of 10 times the amount of the fluoride ion-containing compound.

The compound of Formula 1 and the compound of Formula 2 may be simply mixed or only contact with each other, thereby obtaining 1-MCP. A process of preparing 1-MCP by a reaction between the 1-MCP precursor of Formula 1 and the fluoride ion-containing compound of Formula 2 is disclosed (J. Am. Chem. Soc., 113(1991), 5084-5085; J. Am. Chem. Soc., 113(1991), 7980-7984; Tetrahedron Lett. 36(1995), 3457-3460; Tetrahedron Lett. 16(1975) 3383-3386; J. Org. Chem. 65 (2000), 6217-62222; J. Chem. Soc. Perkin Trans 1, 1993, 945).

1 to 3 equivalent weight of the 1-MCP precursor may be used based on 1 equivalent weight of the fluoride ion-containing compound. When 2 equivalent weight or more of the 1-MCP precursor is used, 1-MCP may be produced in as large amount as possible within 1 hour without unreacted materials.

BEST MODE FOR CARRYING OUT THE INVENTION

One or more embodiments of the present invention will now be described more fully with reference to the following examples. However, these examples are provided only for illustrative purposes and are not intended to limit the scope of the present invention.

Example 1

Synthesis of 1-methylcyclopropene from (trans)-1-methyl-1-(methanesulfonyloxy)-2-(butyldimethylsilyl)cyclopropane (1) Synthesis of (trans)-1-methyl-1-hydroxy-2-(butyldimethylsilyl)cyclopane 2.02 g of magnesium and 30 ml of ethyl ether were placed in a 100 ml three-neck round bottom flask, and 6.3 g of 2-chloropropane was slowly added thereto to prepare a Grignard solution. Meanwhile, 10.7 g of titanium (IV) isopropoxide and 5.4 g of vinylbutyldimethylsilane were placed in another 100 ml three-neck round bottom flask cooled to −78° C., and the above-prepared Grignard solution was gradually added thereto for 30 minutes. The obtained reaction solution was heated to −50° C. and then vigorously stirred for 2 hours. 3.5 g of ethyl acetate was slowly added over 30 minutes, while the reaction solution was maintained at −50° C. The reaction solution was heated to −20° C., vigorously stirred for 1 hours, heated to 0° C., and then vigorously stirred for another 1 hour. The reaction solution was heated to room temperature and 7 ml of saturated brine was added to the solution. The resulting solution was filtered through Celite which was then thoroughly washed once more with 20 ml of ether. The filtrate was dried over anhydrous magnesium sulfate and was concentrated by the evaporation of solvent at a low temperature of 30° C. or less. The resulting concentrate was distilled (35-50° C./0.1 mmHg) to obtain 1-methyl-1-hydroxy-2-(butyldimethylsilyl)cyclopropane as a mixture of two isomers, i.e., trans and cis isomers, at a mixing ratio of about 3:1. In the mixture of two isomers, a major isomer is the trans isomer. In this regard, the mixture of two isomers may be used as it is, but, the trans isomer was separated therefrom using silica gel in order to identify the structure thereof. Results of $^1$H-NMR and $^{13}$C-NMR for the trans isomer of the mixture are given below.

$^1$H NMR(CDCl$_3$, δ) 2.896 (1H, b, —OH), 1.413 (3H, s), 1.299 (4H, m), 0.945 (1H, dd, J=4.2, 11.9 Hz), 0.863 (t, 3H, J=6.8 Hz), 0.506 (2H, m), 0.337 (1H, dd, J=4.2, 8.5 Hz), 0.004 (1H, dd, J=8.5, 11.9 Hz), −0.036 (3H, s), −0.069 (3H, s).

$^{13}$C NMR(CDCl$_3$, δ) 56.044, 26.545, 26.078, 23.597, 18.107, 15.773, 13.754, 13.070, −2.738, −3.026.

(2) Synthesis of (trans)-1-methyl-1-(methanesulfonyloxy)-2-(butyldimethylsilyl)cyclopropane 1.9 g of (trans)-1-methyl-1-hydroxy-2-(butyldimethylsilyl)cyclopropane prepared according to Example 1(1) was dissolved in 15 ml of dichloromethane and 2.3 g of triethylamine was added thereto. The reaction solution was cooled to 0° C., 1.3 g of methanesulfonyl chloride was slowly added to the reaction solution, and the resulting reaction solution was vigorously stirred for 1 hour. 5 ml of saturated NaHCO$_3$ was added to the stirred reaction solution, thereby completing a reaction therebetween. After the reaction was completed, an organic layer was separated from the resultant reaction solution and then dried with anhydrous magnesium sulfate, and the resultant product was concentrated by the evaporation of solvent at a low temperature of 30° C. or less. Although the concentrate may be used directly, it was finely purified by vacuum distillation (65~70° C./0.1 mmHg) to obtain trans-1-methyl-1-(methanesulfonyloxy)-2-(butyldimethylsilyl)cyclopropane. Results of $^1$H-NMR and $^{13}$C-NMR for the trans isomer are given below.

$^1$H NMR(CDCl$_3$, δ) 2.953 (3H, s), 1.684 (3H, s), 1.386 (1H, dd, J=3.2, 10.8 Hz), 1.31 (4H, m), 0.875 (t, 3H, J=6.8 Hz), 0.566 (3H, m), 0.523 (1H, dd, J=4.2, 8.6 Hz), 0.037 (3H, s), −0.015 (3H, s).

$^{13}$C NMR(CDCl$_3$, δ) 67.207, 39.923, 26.396, 25.768, 21.527, 15.899, 15.255, 13.665, 11.661, −3.125, −3.401.

(3) Synthesis of 1-methylcyclopropene

First, 50 ml plastic vessels made of polyethylene were prepared for use as a first vessel, a second vessel, and a third vessel, respectively. The plastic vessels were coupled with a cap unit of a 1-MCP generating apparatus such that except for their inlets and outlets, they were sealed. Tubes were inserted into the inlets and outlets of the second vessel, the first vessel, and the third vessel such that the outlet of the second vessel was connected to the inlet of the first vessel, and the outlet of the first vessel was connected to the inlet of the third vessel. 6.0 g of tetrabutylammonium fluoride (TBAF) was mixed with 9.0 g of DMF to obtain a 40% TBAF-DMF solution, and the TBAF-DMF solution was injected into the second vessel. 1.33 g of trans-1-methyl-1-(methanesulfonyloxy)-2-(butyldimethylsilyl)cyclopropane as a 1-MCP precursor was injected into the first vessel and around the first vessel was maintained at 30° C. by using a thermostat. 15 ml of 2M NaOH aqueous solution was injected into the third vessel.

Afterwards, an electric control device was connected to an air compressor (manufacturer: DAE KWANG ELECTRONIC CO., Product Name: electric bubble generator for aquarium fish, Model Name: DK-20), and air was constantly flowed to the second vessel at a flow rate of approximately 150 ml/min for 30 minutes (total amount of air used: 4,500 ml). A gas that had been discharged via a filter of the third vessel from the first vessel was collected using 10 dl polyethylene bag, and constituents of the gas were analyzed using a GC/MS analyzer and the concentration of 1-MCP was analyzed using GC/FID. The gas analyzed using the GC/MS analyzer was confirmed to be 1-methylcyclopropene (1-MCP, molecular weight: 54). Also, ultra small amounts of ethylene, 1-methylcyclopropane, and butyldimethylfluorosilane were observed, but their amounts were all less than 0.1%. In this regard, 1-MCP is itself unstable and thus is not suitable for long-term storage. Thus, the concentration of 1-MCP was analyzed using 2-methylpropene (isobutylene: Sigma-Aldrich 295469, purity>99.0%) as a standard sample, and the concentration of 1-MCP collected was 19,000 ppm(v/v).

Example 2

First, 50 ml plastic vessels made of polyethylene were prepared for use as a first vessel, a second vessel, and a third vessel, respectively. The plastic vessels were coupled with a cap unit of a 1-MCP generating apparatus such that except for their inlets and outlets, they were sealed. Tubes were inserted into the inlets and outlets of the second vessel, the first vessel, and the third vessel such that the outlet of the second vessel was connected to the inlet of the first vessel, and the outlet of the first vessel was connected to the inlet of the third vessel.

6.0 g of TBAF was mixed with 9.0 g of DMSO to obtain a 40% TBAF-DMSO solution, and the TBAF-DMSO solution was injected into the second vessel. 1.33 g of trans-1-methyl-1-(methanesulfonyloxy)-2-(butyldimethylsily)cyclopropane prepared in the same manner as in Example 1, as a 1-MCP precursor was injected into the first vessel and around the first vessel was maintained at 30° C. by using a thermostat. 15 ml of 2M NaOH aqueous solution was injected into the third vessel.

Afterwards, an electric control device was connected to an air compressor (manufacturer: DAE KWANG ELECTRONIC CO., Product Name: electric bubble generator for aquarium fish, Model Name: DK-20), and air was constantly flowed to the second vessel at a flow rate of approximately 150 ml/min for 60 minutes (total amount of air used: 9.0 dl). A gas that had been discharged via a filter of the third vessel from the first vessel was collected using 10 dl polyethylene bag, and constituents of the gas were analyzed using a GC/MS analyzer and the concentration of 1-MCP was analyzed using GC/FID. The gas analyzed using the GC/MS analyzer was confirmed to be 1-MCP (molecular weight: 54). Also, ultra small amounts of ethylene, 1-methylcyclopropane, and butyldimethylfluorosilane were observed, but their amounts were all less than 0.1%. In this regard, 1-MCP is itself unstable and thus is not suitable for long-term storage. Thus, the concentration of 1-MCP was analyzed using 2-methylpropene (isobutylene: Sigma-Aldrich 295469, purity>99.0%) as a standard sample, and the concentration of 1-MCP collected was 11,000 ppm(v/v).

Examples 3 Through 6

First, 50 ml plastic vessels made of polyethylene were prepared for use as a first vessel, a second vessel, and a third vessel, respectively. The plastic vessels were coupled with a cap unit of a 1-MCP generating apparatus such that except for their inlets and outlets, they were sealed. Tubes were inserted into the inlets and outlets of the second vessel, the first vessel, and the third vessel such that the outlet of the second vessel was connected to the inlet of the first vessel, and the outlet of the first vessel was connected to the inlet of the third vessel.

4.0 g of TBAF was mixed with 6.0 g of DMF to obtain a 40% TBAF-DMF solution, and the TBAF-DMF solution was injected into the second vessel. 1.33 g of trans-1-methyl-1-(methanesulfonyloxy)-2-(butyldimethylsilyl)cyclopropane prepared in the same manner as in Example 1, as a 1-MCP precursor was injected into the first vessel and around the first vessel was maintained at 30° C. by using a thermostat. 15 ml of saturated Na$_2$CO$_3$ aqueous solution was injected into the third vessel.

Afterwards, a flow rate of an air compressor (manufacturer: DAE KWANG ELECTRONIC CO., Product Name: electric bubble generator for aquarium fish, Model Name: DK-20) was adjusted to constantly flow air to the second vessel for 20 minutes or 40 minutes. A gas that had been discharged via a filter of the third vessel from the first vessel was collected using 10 dl polyethylene bag, and constituents of the gas were analyzed using a GC/MS analyzer and the concentration and purity of 1-MCP were analyzed using GC/FID. The gas analyzed using the GC/MS analyzer was confirmed to be 1-MCP (molecular weight: 54). In this regard, 1-MCP is itself unstable and thus is not suitable for long-term storage. Thus, the concentration of 1-MCP was analyzed using 2-methylpropene (isobutylene: Sigma-Aldrich 295469, purity>99.0%) as a standard sample, and the purity of 1-MCP generated for each flow rate of air is shown in Table 1 below.

TABLE 1

|  | Flow rate to air | Temperature of vessel | Generation time | Purity of 1-MCP |
|---|---|---|---|---|
| Example 3 | 100 ml/min | 40° C. | 20 min | 99.9% |
| Example 4 | 100 ml/min | 40° C. | 40 min | 99.9% |
| Example 5 | 200 ml/min | 40° C. | 20 min | 99.5% |
| Example 6 | 200 ml/min | 40° C. | 40 min | 98.8% |

Examples 7 Through 10

First, 50 ml plastic vessels made of polyethylene were prepared for use as a first vessel, a second vessel, and a third vessel, respectively. The plastic vessels were coupled with a cap unit of a 1-MCP generating apparatus such that except for their inlets and outlets, they were sealed. Tubes were inserted into the inlets and outlets of the second vessel, the first vessel, and the third vessel such that the outlet of the second vessel was connected to the inlet of the first vessel, and the outlet of the first vessel was connected to the inlet of the third vessel.

4.0 g of TBAF was mixed with 6.0 g of DMSO to obtain a 40% TBAF-DMSO solution, and the TBAF-DMSO solution was injected into the second vessel. 1.33 g of trans-1-methyl-1-(methanesulfonyloxy)-2-(butyldimethylsilyl)cyclopropane prepared in the same manner as in Example 1, as a 1-MCP precursor was injected into the first vessel and a temperature around the first vessel was varied using a thermostat, and under these conditions, the synthesis of 1-MCP was observed. 15 ml of saturated $Na_2CO_3$ aqueous solution was injected into the third vessel.

Afterwards, air was constantly flowed to the second vessel at a flow rate of 200 ml/min for 60 minutes (total amount of air used: 12,000 ml) by using an air compressor (manufacturer: DAE KWANG ELECTRONIC CO., Product Name: electric bubble generator for aquarium fish, Model Name: DK-20). A gas that had been discharged via a filter of the third vessel from the first vessel was collected using 20 dl polyethylene bag, and constituents of the gas were analyzed using a GC/MS analyzer and the concentration of 1-MCP was analyzed using GC/FID. The gas analyzed using the GC/MS analyzer was confirmed to be 1-MCP (molecular weight: 54). In this regard, 1-MCP is itself unstable and thus is not suitable for long-term storage. Thus, the concentration of 1-MCP was analyzed using 2-methylpropene (isobutylene: Sigma-Aldrich 295469, purity>99.0%) as a standard sample, and the purity and concentration of 1-MCP collected for each temperature of vessel are shown in Table 2 below.

TABLE 2

|  | Temperature of vessel | Flow rate to air | Generation time | Concentration of 1-MCP | Purity of 1-MCP |
|---|---|---|---|---|---|
| Example 7 | 20° C. | 200 ml/min | 60 min | 8,200 ppm(v/v) | 99.93% |
| Example 8 | 30° C. | 200 ml/min | 60 min | 8,900 ppm(v/v) | 99.93% |
| Example 9 | 40° C. | 200 ml/min | 60 min | 8,900 ppm(v/v) | 99.94% |
| Example 10 | 50° C. | 200 ml/min | 60 min | 9,000 ppm(v/v) | 98.3% |

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A 1-methylcyclopropene generating apparatus comprising:
   a first vessel comprising a 1-methylcyclopropene precursor;
   a second vessel comprising a fluoride ion-containing compound solution that reacts with the 1-MCP precursor to produce 1-methylcyclopropene;
   a third vessel comprising a filter for removing byproducts except for 1-methylcyclopropene from the reaction product; and
   a carrier gas that is introduced into the second vessel to transfer the fluoride ion-containing compound solution into the first vessel so that the 1-methylcyclopropene precursor and the fluoride ion-containing compound solution react with each other to produce a reaction product including 1-methylcyclopropene in the first vessel, wherein the reaction product is discharged to the outside through the third vessel,
   wherein the first vessel, the second vessel and the third vessel comprise inlets and outlets, which are positioned in an upper side of the first vessel, the second vessel and the third vessel, respectively;
   wherein the second vessel, where the carrier gas is introduced, comprises the inlet including a tube adjacent to the upper side and the outlet including a tube adjacent to a bottom side;
   wherein the first vessel comprises the inlet including a tube adjacent to the upper side and the outlet including a tube adjacent to the upper side and not being adjacent to the bottom side of the first vessel;
   wherein the third vessel comprises the inlet including a tube adjacent to a bottom side and the outlet including a tube adjacent to the upper side;
   wherein the first vessel, the second vessel and the third vessel, or the second vessel, the first vessel and the third vessel are sequentially connected to one another through the tubes; and
   wherein as the carrier gas moves from the second vessel, where the carrier gas is introduced, to third vessel, the carrier gas discharges a reaction product including 1-methylcyclopropene produced in the first vessel to the outside through the third vessel so that transfer of reactants, reaction therebetween, and discharge and purification of the reaction product are performed in an integrated manner.

2. The apparatus of claim 1, wherein the first vessel, the second vessel, and the third vessel are detachably attached.

3. The apparatus of claim 1, wherein at least one of the tubes has an internal diameter ranging from 1.0 to 3.0 mm, and the carrier gas is introduced into the first vessel or the second vessel through the tube at a flow rate of 10 ml/min to 1,000 ml/min.

4. The apparatus of claim 1, further comprising a case in which the first vessel, the second vessel, and the third vessel are mounted.

5. The apparatus of claim 1, wherein the 1-methylcyclopropene precursor is a β-halocyclopropylsilane derivative represented by Formula 1 below:

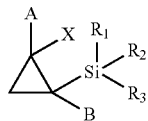

<Formula 1> where A is a methyl group;

B is a hydrogen atom;

X is a halogen atom or a leaving group containing any one selected from an oxygen atom, a sulfur atom, a nitrogen atom, and a phosphorus atom; and each of $R_1$, $R_2$, and $R_3$ is independently one of a hydrogen atom, a $C_1$-$C_{10}$ alkyl group, a $C_6$-$C_{10}$ aryl group, a $C_1$-$C_{10}$ alkoxy group, and a halogen atom.

6. The apparatus of claim 1, wherein the fluoride ion-containing compound is a compound represented by Formula 2 below:

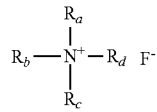

<Formula 2> where each of $R_a$, $R_b$, $R_c$, and $R_d$ is independently a $C_1$-$C_{20}$ alkyl group or a $C_6$-$C_{15}$ aryl group.

7. The apparatus of claim 1, wherein the first vessel or the second vessel further comprises a thermostat.

8. The apparatus of claim 1, wherein the carrier gas is a nitrogen gas or air.

9. The apparatus of claim 1, wherein an amount of the 1-methylcyclopropene precursor is 1 to 3 equivalent weights based on 1 equivalent weight of the fluoride ion-containing compound solution.

10. The apparatus of claim 1, wherein the filter comprises a basic aqueous solution; a basic short-chain alcohol solution; a sponge-type polymer or natural fiber that is impregnated with a basic aqueous solution or a basic short-chain alcohol solution; or an inorganic material.

11. The apparatus of claim 7, wherein the first vessel or the second vessel that comprises the thermostat is maintained at a temperature ranging from 10 to 60° C.

12. The apparatus of claim 1, wherein the fluoride ion-containing compound solution is prepared by dissolving a fluoride ion-containing compound in at least one solvent selected from DMSO, DMF, dimethylacetamide, and 1-methyl-2-pyrrolidone.

13. The apparatus of claim 1, wherein the fluoride ion-containing compound solution has a concentration ranging from 5% to 65%.

* * * * *